United States Patent [19]

Haino

[11] Patent Number: 4,752,974

[45] Date of Patent: Jun. 28, 1988

[54] AIR-FEED TYPE DUST PROTECTIVE HELMET

[75] Inventor: Yoshiaki Haino, Ohmiya, Japan

[73] Assignee: Shigematsu Works Co., Ltd., Tokyo, Japan

[21] Appl. No.: 937,914

[22] Filed: Dec. 4, 1986

[30] Foreign Application Priority Data

May 6, 1986 [JP] Japan .................. 61-66998[U]

[51] Int. Cl.$^4$ ............................................. A42B 3/00
[52] U.S. Cl. ................................ 2/424; 2/171.3; 128/201.24; 128/200.28
[58] Field of Search ............... 2/8, 171.3, 171.4, 424, 2/10; 128/201.24, 201.25, 200.28

[56] References Cited

U.S. PATENT DOCUMENTS

| 2,032,101 | 2/1936 | Sullivan | 128/200.28 |
| 2,560,215 | 7/1951 | Christensen | 128/200.28 |
| 2,688,962 | 9/1954 | Summers | 2/8 X |
| 3,223,086 | 12/1965 | Denton | 128/201.24 |
| 3,813,696 | 6/1974 | Yeager | 2/171.3 |
| 3,881,478 | 5/1975 | Rosendahl et al. | 2/171.3 X |
| 4,280,491 | 7/1981 | Berg et al. | 2/171.3 X |
| 4,442,551 | 4/1984 | Hellberg | 2/424 X |
| 4,571,741 | 2/1986 | Guillaumot | 2/8 |
| 4,676,236 | 6/1987 | Piorkowski et al. | 128/201.25 X |

FOREIGN PATENT DOCUMENTS

| 1201975 | 1/1960 | France | 128/200.28 |
| 233265 | 2/1986 | German Democratic Rep. | 2/171.3 |
| 145816 | 6/1954 | Sweden | 2/8 |
| 835200 | 5/1960 | United Kingdom | 128/200.28 |
| 570359 | 8/1977 | U.S.S.R. | 2/424 |

*Primary Examiner*—Peter Nerbun
*Attorney, Agent, or Firm*—Larson and Taylor

[57] ABSTRACT

An air-feed type protective helmet includes a cap body to which a face shield is rotatably mounted for movement between a lower use position and an upper non-use position. In order to feed clean air to a space provided between the wearer's face and the face shield, a front visor portion is provided which extends from one lateral side to the other lateral side. This front visor portion includes an inner wall and an outer wall which are integrally formed with the cap body and which have an opening therebetween at lower edges thereof. A bottom wall closes the opening between the inner wall and outer wall to define an air passage. An air outlet is provided in the bottom wall. An air pipe connector is located on one of the lateral sides and is in fluid communication with the air passage. The air pipe connector includes an air pipe connection to which a source of clean air is connectable. Preferably, the air passage has lateral openings at each lateral side, one of which is closed by the air connector and the other of which is closed by an air passage closing member. In the preferred embodiment, the bottom wall, the air pipe connector, and the air passage closing member are all detachably mounted to the cap body.

1 Claim, 3 Drawing Sheets

AIR-FEED TYPE DUST PROTECTIVE HELMET

FIELD OF THE INVENTION

The present invention relates to a labor, safety and hygienic protective device for protecting a head, the face and the respiratory organs of a human being, and more specifically to an air-feed type dust protective helmet which can protect the respiratory organs.

DESCRIPTION OF THE PRIOR ART

Air-feed type dust protective helmets for simultaneously protecting a head, the face and the respiratory organs of an operator have been well known, for example, such as an air-feed type dust protective helmet manufactured and sold by RACAL SAFETY LIMITED in England. FIG. 7 illustrates a construction of the air-feed type dust protective helmet. In FIG. 7, reference numeral 31 designates a cap body, 32 a face shield mounted rotatably up and down on the cap body 31, 33 an electric fan mounted at the rear of and internally of the cap body, 34 a primary filter mounted on an intake opening of the electric fan, 35 a bag-like main filter mounted on an exhaust opening of the electric fan, 36 a seal member for preventing air from flowing sideways passing through a clearance between the cap body and the head, and 37 face seal members mounted on opposite side edges of the face shield to close the clearance between the shield and the face. When the electric fan 33 is actuated, outside air is sucked from the intake opening through the primary filter 34 and fed into the bag-like main filter 35 encased between the cap body 31 and the head. The air is then filtrated by the main filter and thereafter fed between the face shield 32 and the face, after which the air is discharged outside through an open clearance at the lower end thereof. Accordingly, the wearer of the well-known air-feed type dust protective helmet can protect his head and face from possible damages caused by flying or falling things, and even in the working environment involving much dust, the operator can work while breathing clean air.

The helmet is used for the purpose of protecting the head of a wearer from damages caused by flying and falling things and, from damages resulting from when the user falls, and from an electric shock during electric work. Therefore, the construction, strength, insulation and the like of such helmets are strictly stipulated in laws and regulations of a typical nation. According to the laws and regulations of a typical nation, it is compulsory that a required buffer member is mounted internally of the cap body. However, in the aforesaid known air-feed type dust protective helmet, the main filter is encased between the cap body and the head. Therefore, it is impossible to mount the buffer member for damping protection internally of the cap body. Thus, the aforesaid known air-feed type dust protective helmet is not allowed for use as such a protective helmet.

SUMMARY OF THE INVENTION

It is an object of the present invention to provide an air-feed type dust protective helmet which is officially approved for use as a helmet for protection of flying and falling things, for protection when the user falls and for protection from electric shock (electrically insulated).

The present invention provides an arrangement characterized in that a lower peripheral edge portion of a cap body of an air-feed type dust protective helmet is formed into a double wall comprising an inner wall and an outer wall, an air passage is formed over the entire circumference of the lower peripheral edge portion of the cap body or over the required area including a front visor portion thereof, an air outlet is provided in a bottom wall of the front visor portion of said air passage to allow the air within said air passage flow downwardly, and an air pipe connector having an air pipe connection is provided in a suitable location of said air passage.

According to the present invention, there is provided an air-feed type dust protective helmet which is officially approved for protective use wherein a protective buffer member is inserted internally of the cap body since the internal structure of the cap body is exactly the same as that of the cap body of a conventional helmet.

One embodiment of the air-feed type dust protective helmet according to the present invention will be described hereinafter in connection with the accompanying drawings.

BRIEF DESCRIPTION OF THE DRAWINGS

FIG. 2 is an exploded bottom view of the dust protective helmet shown in FIG. 1;

DETAILED DESCRIPTION OF THE INVENTION

Figure 1:
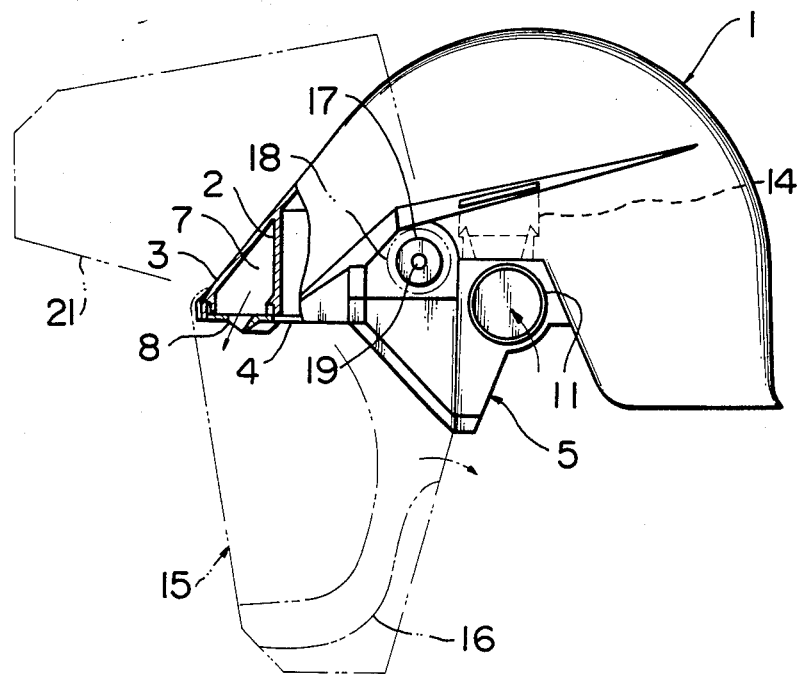
FIG. 1 is a side view in section showing essential parts of an air-feed dust protective helmet according to the present invention with a face shield, a wearing string and the like removed.
Figure 3:
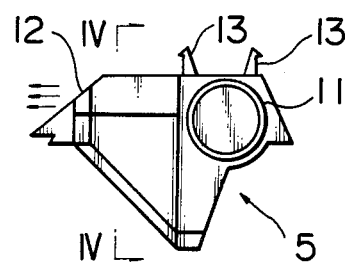
FIG. 3 is a front view of an air-feed pipe connector.
Figure 4:
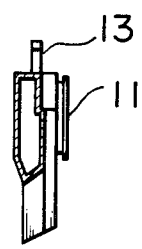
FIG. 4 is a sectional view taken on line IV—IV of FIG. 3.
Figure 5:
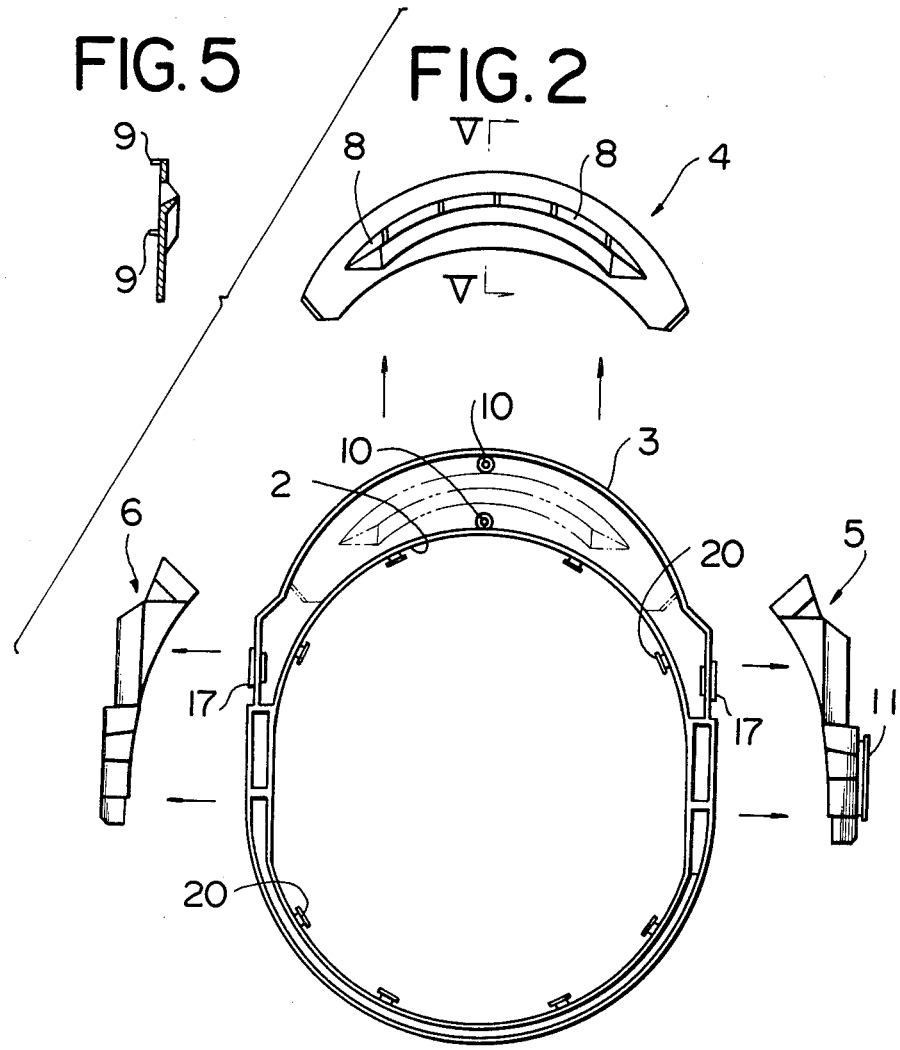
FIG. 5 is a sectional view taken on line V—V of FIG. 2.
Figure 6:
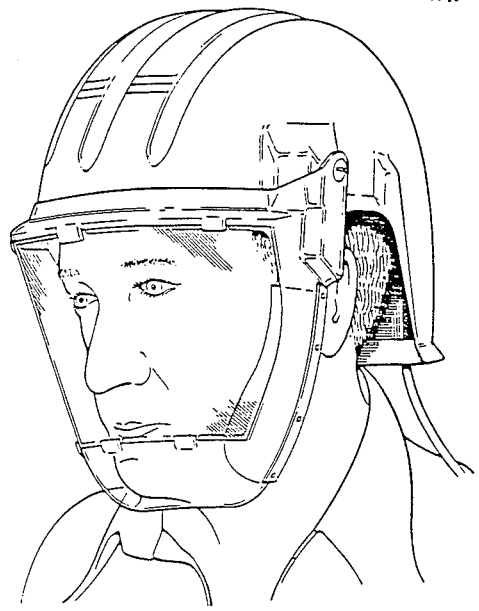
FIG. 6 is a perspective view showing the state wherein a conventional air-feed type dust protective helmet is worn.
Figure 7:
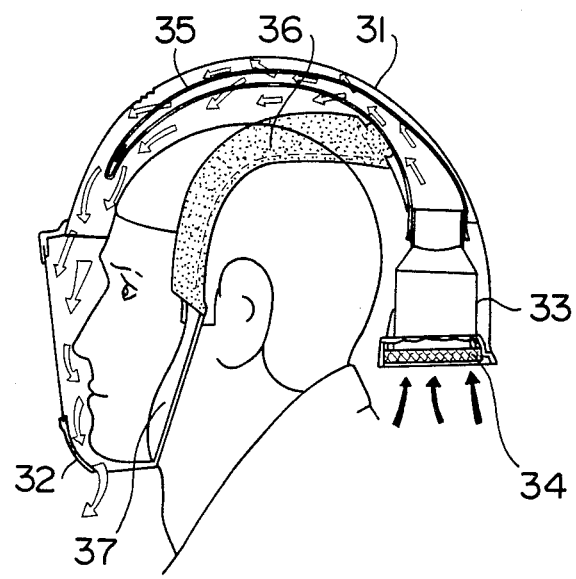
FIG. 7 is an explanatory view for the construction of the dust protective helmet shown in FIG. 6.

Referring to FIGS. 1 and 2, a reference numeral 1 designates a cap body in which a lower peripheral edge portion generally in a front half portion thereof is integrally formed with an inner wall 2 and an outer wall 3. In the lower end edges of the inner wall 2 and the outer wall 3, a front visor portion, a lefthand portion and a righthand portion are closed by an air-feed plate 4, an air pipe connector 5 and an air passage closing member 6, respectively, an air passage 7 being formed between the inner wall 2 and the outer wall 3. The air-feed plate 4 having an air outlet 8 is mounted on the cap body by snapping projections 9 provided on the upper surface thereof into mounting holes 10 formed in the inner wall 2 and outer wall 3 of the cap body. The air-feed pipe connector 5, which is formed into a closed hollow configuration (see FIGS. 3 and 4) except an air-feed connection 11 and an exhaust opening 12, is mounted by fitting into and engaging engageable projections 13 integrally formed with engageable holes 14 provided in the cap body 1. The air passage closing member 6, which is generally the same shape as the air pipe connector 5, is likewise mounted on the cap body 1. The closing member 6 is different from the air pipe connector 5 in that the former is not provided with an air-feed connecting opening and an air exhaust opening but the whole body is formed into a closed hollow configuration. In mounting the air-feed plate 4 and the air pipe connector 5 on the cap body, joining surfaces are adhered to each other by adhesives or the like in addition to the means for snapping the projections 9 or engaging projections 13 into the mounting holes 10 or engaging means such as the engaging hole 14 of the cap body 1. In the figures, reference numeral 15 designates a face shield in its using position, 16 a face seal member for closing a clearance between the face shield and the face mounted over both side edges and a lower edge of the aforesaid face shield, 17 support shafts provided on left and right sides of the cap body 10 to rotatably mount the face shield on the cap body 1, 18 a handscrew for mounting the face shield, 19 a tapped hole for threadedly receiving said hand-screw, 20 a pin for mounting a hammock in contact with the head of a wearer, and 21 a face shield rotated to the unused position.

The operation will now be described. The forward end of the air pipe extending from a dust filtration and air-feed device worn on the waist or the like of the human body or a stationary-type clean air feed device is connected to the air pipe connection 11. When the dust filtration and air feed device or the clean air feed device is actuated, the clean air flows into the air passage 7 of the cap body 1 through the connector 5 and flows out of the outlet 8 of the air-feed plate into and between the face shield 15 and the face. Air between the face shield and the face passes through a cut portion of the face seal member 16 located above both the side edges of the face shield and is discharged into the outside air. If the quantity of air from the air-feed device is in a level above a predetermined amount, the interior of the face shield 15 is always maintained under positive pressure, and therefore a person wearing the above-described dust protective helmet may perform his work in the environment where dust is floating while always pleasantly breathing clean air.

While in the above-described embodiment, only the front half portion of the lower peripheral edge portion of the cap body has been in the form of a double wall and the air passage has been formed only in the front half portion, it is to be noted that the whole lower peripheral edge portion of the cap body can be formed into a double wall and an air passage can be formed over the whole circumference, the air-feed pipe being connected to the air passage at the rear of the cap body.

What is claimed is:

1. An air-feed type dust protective helmet comprising:
    a cap body having a front, a back, a top, and two lateral sides;
    a face shield which is rotatably mounted to said cap body such that said face shield is movable between a lower use position adjacent the front of said cap body and an upper non-use position; and
    an air feeding means for feeding clean air to a space provided between a wearer's face and said face shield when said face shield is in the lower use position, said air feeding means including,
    (a) a front visor portion located above a frontal lower peripheral edge portion of said cap body and extending from one lateral side to the other lateral side, said front visor portion having an inner wall and an outer wall which are integrally formed with said cap body and which form an opening therebetween at lower edges thereof from one lateral side to the other,
    (b) a bottom wall which closes the opening between said inner wall, said outer wall and said lateral sides such that an air passage is defined between said bottom wall, said inner wall, and said outer wall,
    (c) an air outlet provided in said bottom wall,
    (d) an air pipe connector located on one of said lateral sides of said cap body which is in fluid communication with said air passage, said air pipe connector including an air pipe connection to which a source of clean air is connectable, and
    (e) lateral openings at each lateral side of said air passage, one lateral opening being closed by said air pipe connector and the other opening being closed by an air passage closing member.

* * * * *